United States Patent [19]

Anderson

[11] Patent Number: 5,062,839
[45] Date of Patent: Nov. 5, 1991

[54] DISPOSABLE TRAINING PANTY WITH CONTROLLED WETNESS RELEASE

[76] Inventor: Dora Anderson, 28 Metamora Crescent, London, Ontario, Canada, N6G 1R3

[21] Appl. No.: 497,129

[22] Filed: Mar. 21, 1990

[30] Foreign Application Priority Data

Sep. 29, 1989 [CA] Canada .................................. 614631

[51] Int. Cl.⁵ ............................................. A61F 13/15
[52] U.S. Cl. .................................. 604/385.1; 604/396
[58] Field of Search ................... 604/396, 385.1, 385.2

[56] References Cited

U.S. PATENT DOCUMENTS

| | | |
|---|---|---|
| 1,485,001 | 2/1924 | Wills . |
| 2,101,453 | 12/1937 | Rhodes . |
| 2,510,665 | 6/1950 | Sonnenberg . |
| 2,515,737 | 7/1950 | Schwarzberger . |
| 2,714,889 | 8/1955 | Chambers . |
| 2,748,772 | 6/1956 | Titone et al. . |
| 2,770,237 | 11/1956 | Starr . |
| 2,801,632 | 8/1957 | Burner et al. . |
| 3,599,640 | 8/1971 | Larson . |
| 3,756,878 | 9/1973 | Willot .................................. 156/70 |
| 3,882,871 | 5/1975 | Taniguchi . |
| 4,205,679 | 6/1980 | Repke et al. . |
| 4,397,646 | 8/1983 | Daniels et al. ...................... 604/381 |
| 4,560,381 | 12/1985 | Southwell ........................... 604/396 |
| 4,619,649 | 10/1986 | Roberts ................................ 604/396 |
| 4,641,381 | 2/1987 | Heran et al. ...................... 604/392 X |
| 4,671,793 | 6/1987 | Hults et al. ...................... 604/385 R |
| 4,743,239 | 5/1988 | Cole .................................. 604/385.1 |
| 4,743,239 | 5/1988 | Cole .................................. 604/385 R |
| 4,887,602 | 12/1989 | O'Leary ........................ 604/385.2 X |
| 4,895,568 | 1/1990 | Enloe ................................ 604/385.2 |
| 4,909,804 | 3/1990 | Douglas ............................. 604/385.2 |

*Primary Examiner*—Randall L. Green
*Assistant Examiner*—David H. Willse
*Attorney, Agent, or Firm*—Basile and Hanlon

[57] ABSTRACT

There is provided a disposable training panty having a permeable outer covering. An inner absorbent portion is secured to the outer covering. In the event a young child has a bowel or bladder accident the majority of the wetness generated is absorbed by the inner absorbent portion. However, the inner absorbent portion does not fully absorb the child's wetness and some wetness leaks onto the permeable outer covering. Therefore the panty releases to the permeable outer covering, to a controlled extent, unabsorbed wetness. Because the outer covering is permeable the wetness quickly cools and the outer covering clings to the child's skin causing the child to feel the discomfort of both the wetness and the coldness promptly.

7 Claims, 4 Drawing Sheets

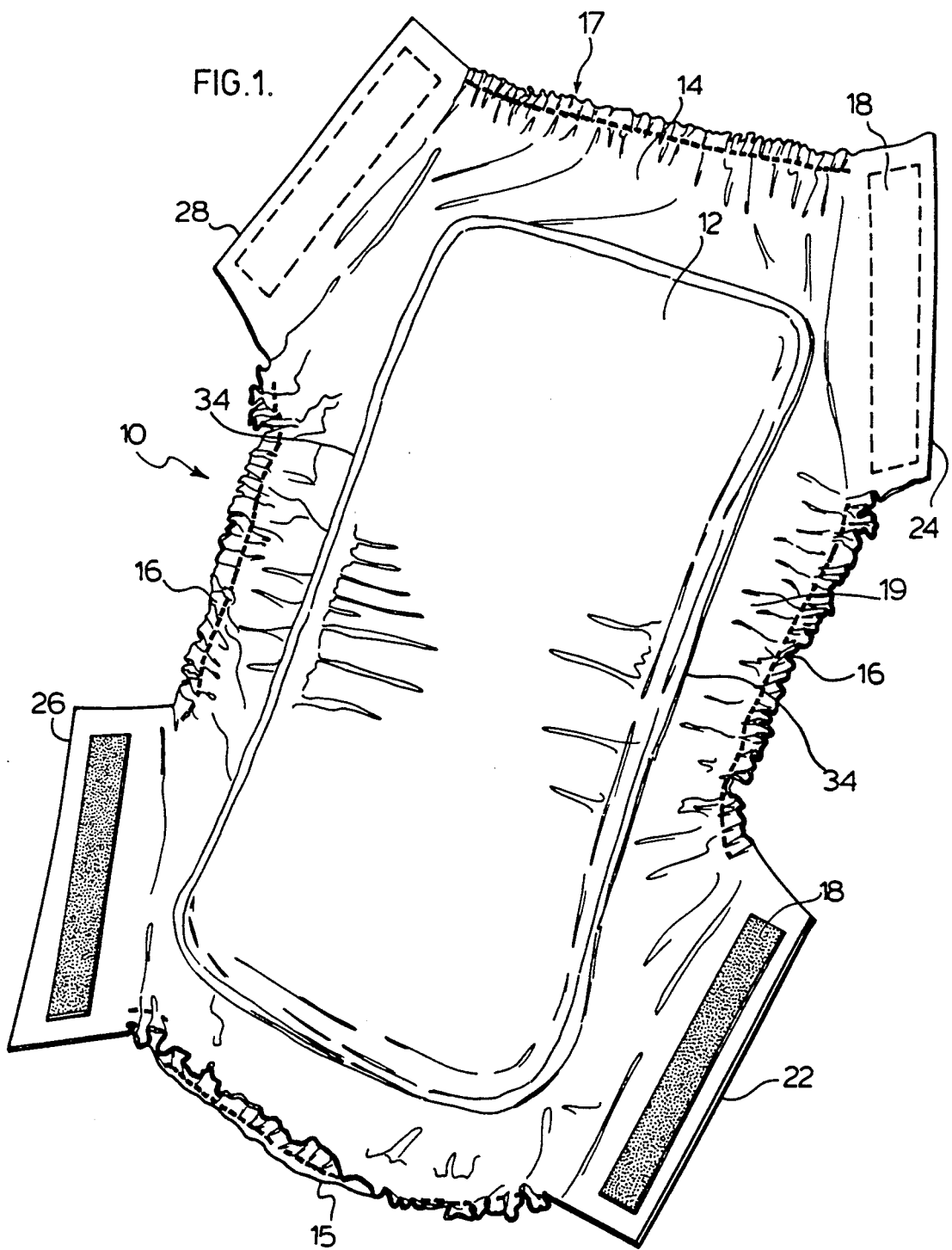

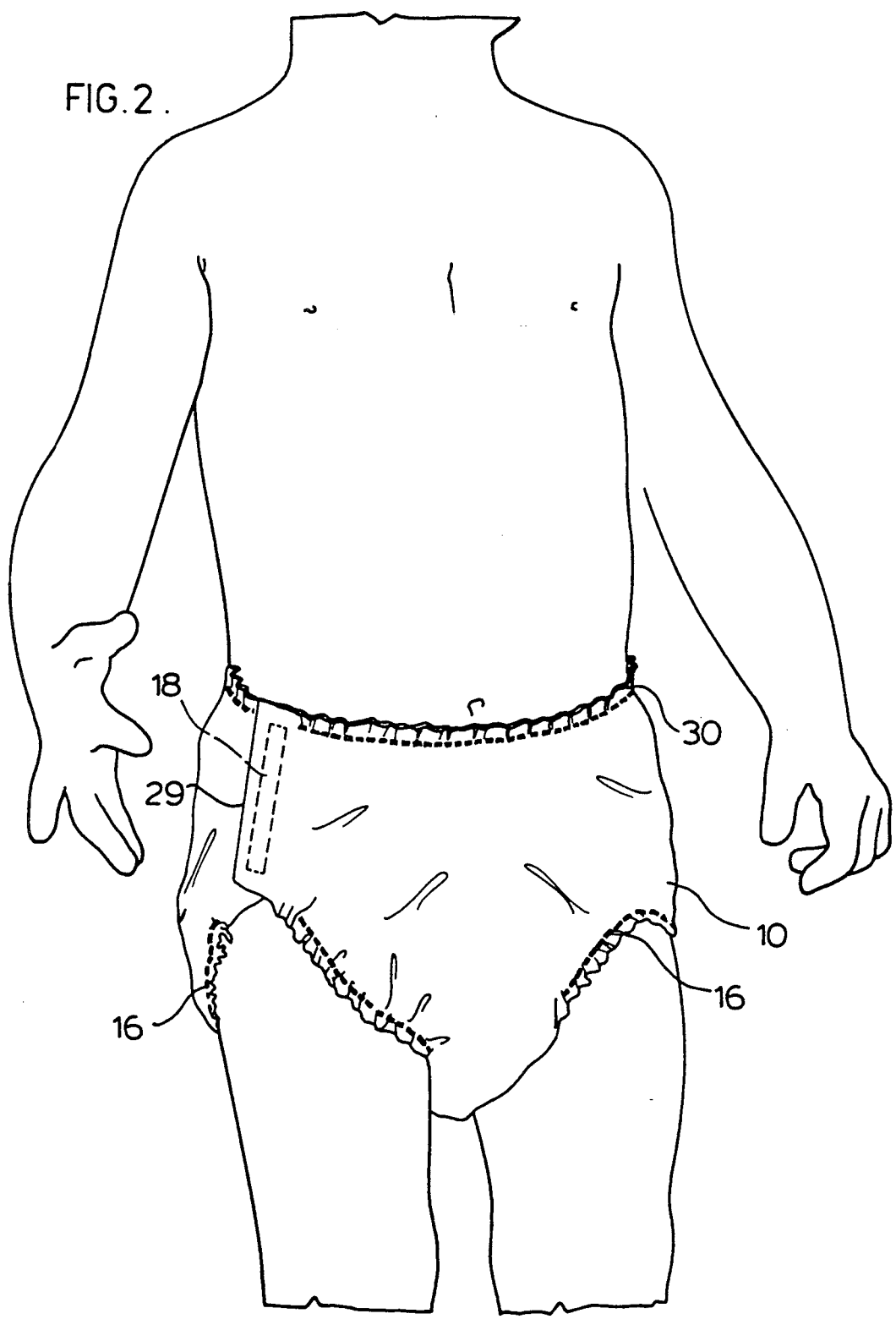

DISPOSABLE TRAINING PANTY WITH CONTROLLED WETNESS RELEASE

FIELD OF THE INVENTION

This invention relates to disposable training pants for young children.

BACKGROUND OF THE INVENTION

During the period when a young child is being toilet trained it has come to be recognized that a specialized training pant is a critical part of the training process. This has become of even greater importance in recent years as disposable diapers have become more and more technologically advanced in the art of keeping babies feeling warm and dry.

Psychology plays an important role in toilet training a child, and training pants are known to be a beneficial psychological aid in the training process. Three of the most important factors in this process are that the child is old enough, willing to co-operate and free of diapers. Once the first two criteria have been met, the next step is for the child to stop wearing diapers during the day. Diapers hinder the training process in two key ways. An important feature of training pants is that they approximate a normal underpant. Unlike a diaper, the training pant is put on or removed by the child with little or no adult assistance so long as the pant remains unsoiled. The child, therefore, associates the training pant with greater personal independence.

The other problem which diapers pose for the toilet training child is that they are designed to keep the child dry. Traditional cloth diapers were always used in association with a rubber pant. Virtually all present day disposable diapers keep the child feeling warm and comfortable. All diapers effectively operate to keep wetness in and to keep air out. A high degree of absorbency, padding and an impermeable outer layer all combine in a diaper to give the child a sense of warmth and comfort.

In the present invention it has been recognized that an effective training pant allows the child to feel the cold of its wetness in order to alert the child to the discomfort associated with a bowel or bladder accident.

Many prior art attempts have been made at developing a disposable training pant. The most recent of these is, U.S. Pat. No. 4,743,239 (Cole). Cole teaches a disposable training panty which is perforated along the sides to facilitate removal of the panty after the child has either a bowel accident or a bladder accident. By perforating or scoring the sides of the training panty, the panty can be removed without traversing the lengths of the legs of the user thereby reducing the incidents of contamination on the child and in the area surrounding the child. The Cole training panty is fully lined throughout the inside of the diaper with two thicknesses of absorbent layers and has a third thicker layer in the crotch area. The outer lining is a generally waterproof material comprising a moisture barrier.

U.S. Pat. No. 4,619,649 (Roberts) teaches a disposable toddler training panty having a thin plastic outer layer and an inner surface with a comfortable soft inner lining and separable side seams from the waist band to the leg band. The Roberts disposable training pant has an impermeable outer plastic layer fully lined by the soft inner layer.

U.S. Pat. No. 4,671,793 (Hults) teaches a disposable training pant for young children having a plastic outer cover and an inner absorbent lining which is thin at the sides and thick in the middle crotch area. The inner absorbent lining is replaceable and lines the outer moisture impermeable layer fully.

Four other United States patents disclose disposable undergarments: U.S. Pat. No. 3,756,878 (Willot); U.S. Pat. No. 3,599,640 (Larson); U.S. Pat. No. 4,205,679 (Repke); U.S. Pat. No. 2,748,772 (Titone).

An effective training pant should allow the child to feel the cold of its wetness in order to alert the child to the discomfort associated with the bowel or bladder accident. This discomfort will only be readily apparent if the outer material of the training pant is permeable to moisture. This permeability allows the child to feel the coldness of the wetness against its body because when air moves across the wet surface warmth is not retained and the child feels cold. An important aspect of the training panty of the present invention not recognized by the prior art is that it is adapted so that the child readily feels the coldness associated with his or her own wetness after a bowel or bladder accident. Two aspects of the present invention operate to achieve a controlled level of discomfort to alert the child. The first is the presence of a moisture permeable outer covering and the second is that the training panty of the present invention is adapted to release wetness to a controlled extent.

An important psychological feature of a training panty is the closeness with which the panty approximates a normal panty. In the present invention the outer permeable covering is not fully lined by the inner absorbent portion and, therefore, more closely approximates the feel of a normal panty.

It is appreciated that the training panty should look like a normal panty when first put on by the child. However, in the event that the child has a bladder or bowel accident the panty should be readily removable while minimizing any contamination to the child or the surrounding environment. The present invention details an embodiment in which the secured sides of the disposable panty are readily opened for removal in the event of an accident. Since the panty is disposable it can be easily discarded in a sterile manner.

SUMMARY OF THE INVENTION

According to the present invention a disposable training panty is provided which releases wetness to a controlled extent thereby providing all of the benefits of a disposable panty and also facilitating the toilet training process in young children.

According to the present invention, there is provided a disposable training panty adapted to release wetness to a controlled extent, comprising:

(a) an outer permeable covering including a front portion and a back portion the front and back portions being contiguous along a crotch area, (b) an inner absorbent portion secured to the outer covering which does not fully absorb a child's wetness whereby in the event the child has a bowel or bladder accident in the panty the panty releases through the permeable covering to the controlled extent unabsorbed wetness, (c) means for joining the sides of the front and back portions to form side seams the joining means being releasable to permit ready opening of the seams in the event the child has a bowel or bladder accident in the panty, (d) means for securing the panty to a child's waist, and
(e) means for defining leg openings through which a child's legs will extend once the panty is secured to a child.

In accordance with another aspect of the present invention is a disposable panty having side seams formed by loosely basting a pair of ties along the length of the side seams, the ties further comprising means for securing the ties to the panty and means for ready removal of the ties from the panty.

Other and further advantages and features of the invention will be apparent to those skilled in the art from the following detailed description thereof, taken in conjunction with the accompanying drawings.

BRIEF DESCRIPTION OF THE DRAWINGS

FIG. 1 is a perspective view of the disposable training panty fully opened showing the inside of the panty. This embodiment specifically illustrates the use of velcro to secure the sides together;

FIG. 2 illustrates the disposable training panty as viewed from the front of a child wearing the panty;

DETAILED DESCRIPTION OF THE PREFERRED EMBODIMENTS

Figure 3A:
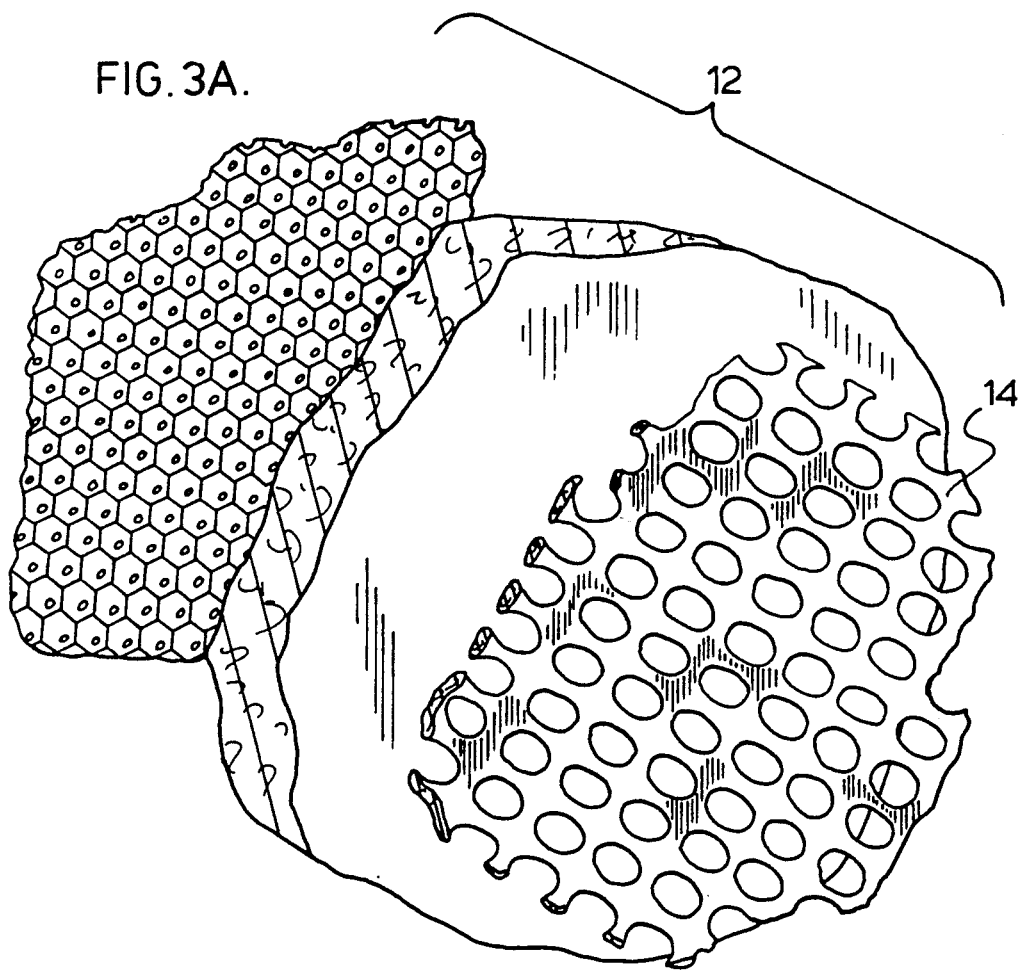
FIG. 3A illustrates the outer permeable covering and the inner absorbent portion.

The principles of a disposable training panty adapted to release wetness to a controlled extent having releasable side seams and a permeable outer covering are demonstrated in accordance with the following preferred embodiments of the invention.

According to a preferred embodiment of the present invention a disposable training pant having a moisture permeable outer covering is provided such that said training pant leaks to a controlled extent when the child has a bowel or bladder accident. The outer covering of the training panty of the present invention is permeable to permit some leakage of wetness in the event of a bowel or bladder accident. This then alerts the child to the accident and causes the child to experience discomfort both physically and psychologically. The absorbent inner portion allows this leakage to occur in a controlled manner such that any contamination to the child's legs is minimized. Preferred embodiments of the present invention can be identified with reference to the Figures.

A disposable training panty 10 is illustrated in FIG. 1 having an outer permeable covering 14 and an inner absorbent portion 12. The width of the inner absorbent portion 12 is narrower than the width of the crotch area 19. The outer permeable cover 14 has a back portion 17 and a front portion 15. The back portion 17 and front portion 15 are contiguous through crotch area 19.

The inner absorbent portion 12 extends partially along the length of the back portion 17 and partially along the length of the front portion 15.

Figure 3B:
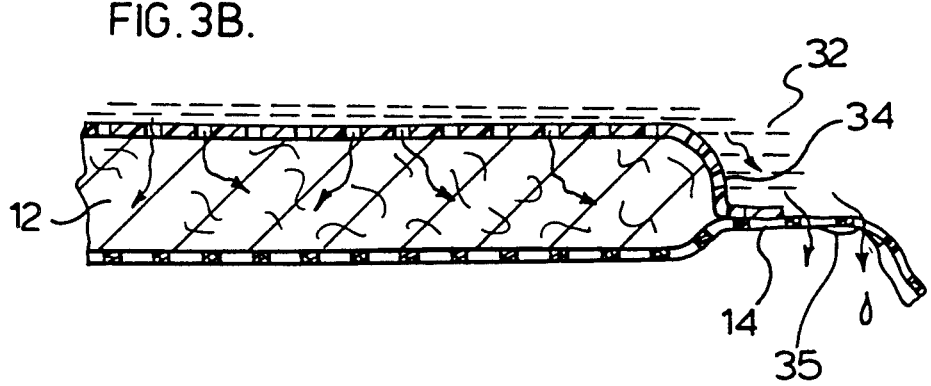
FIG. 3B illustrates the controlled leakage of fluid around the edges of the absorbent material of the inner absorbent portion.

As illustrated in FIG. 3B, the inner absorbent portion 12 is not fully absorbent such that when the child has a bowel or bladder accident wetness leaks away to a controlled extent from the absorbent portion 12 and through the permeable outer covering 14. In one preferred embodiment the wetness 32 leaks around the sides 34 of inner absorbent portion 12 (FIG. 3B). When air passes across the moist surface 35 of the outer covering 14 warmth contained in the moisture 32 is extracted and the child feels cold.

As illustrated in FIG. 1 the inner absorbent portion 12 does not fully cover the inside surface of the outer permeable covering 14. The inner absorbent portion 12 is narrower in width than the width of the crotch area 19. In length, the inner absorbent portion 12 runs through the crotch area 19 extending into the front and back portions 15 and 17 of the panty 10. The edges 34 of the inner absorbent portion 12 are spaced apart from the sides of the panty 10.

The child's skin remains in contact with the outer permeable covering 14 in those areas of the panty 10 which are not lined by the inner absorbent portion 12. When the child has a bowel or bladder accident the wetness 32 is not fully absorbed by the inner absorbent portion 12 and leaks onto the permeable outer covering 14. The permeable outer covering 14 becomes wet 35. Because the outer covering 14 is permeable the wetness is exposed to the air and quickly cools and the wet covering 35 clings to the child's skin causing the child to feel the discomfort of the wetness and coldness.

As illustrated in FIGS. 1 and 2, the sides 24 and 28 of the back portion 17 and the sides 22 and 26 of the front portion 15 have velcro 18 attached to them so that sides 22 and 24 can be joined to form one releasable side seam 29 (FIG. 2) and sides 26 and 28 can be joined to form the other releasable side seam (not shown). In this way the side seams of the panty 10 are secured to approximate the side seams of a normal underpant, however, in the event of an accident the seams are readily released to facilitate removal of the panty without undue contamination.

Figure 4A:
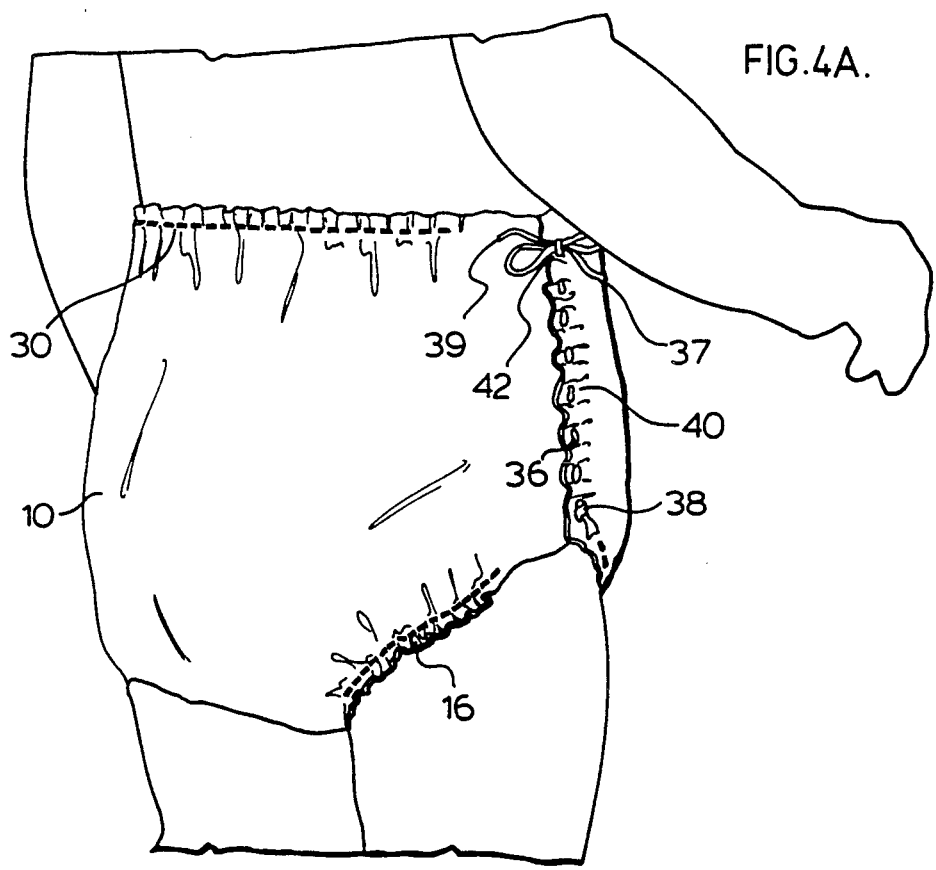
FIGS. 4A and 4B illustrate the disposable training panty as viewed from the back of a child wearing the panty. This embodiment specifically illustrates the use of paired ties to secure the sides together.
Figure 4B:
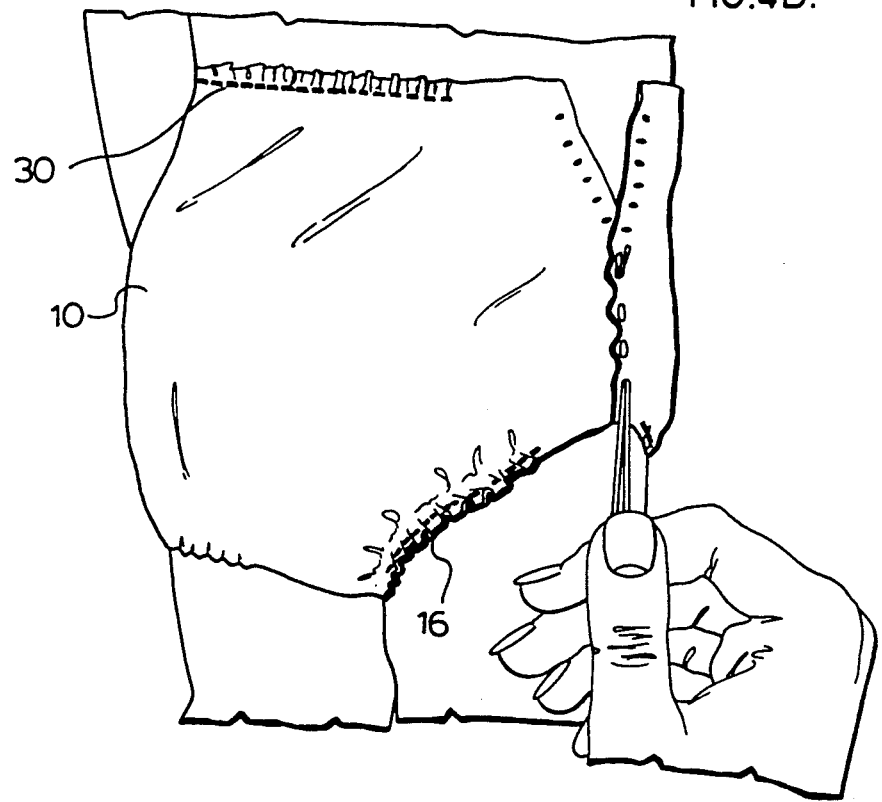

As illustrated in FIGS. 4A and 4B, the side seams of the panty 10 are releasably joined using a pair of ties 37 and 39. The ties are loosely basted 36 through the overlapping front and back sides to secure them together and form a side seam 40. The loose ends of the ties 37 and 39 are tied to form a bow 42 securing the ties in the panty.

In the event of a bowel or bladder accident by the child the ties 37 and 39 are pulled by way of knot 38 and the side seams are readily released detaching the front and back portions from each other as the ties are pulled out. Such a tie mechanism for releasably joining the side seams helps to give the panty the required overall look of a normal underpant.

To secure the panty to the child the waist 30 and leg openings 16 of the panty 10 are elasticized.

It is appreciated that such a disposable panty could be made of any materials having the required characteristics as described herein. Suitable biodegradable materials would be preferred. It is also appreciated that the side seams of this panty could be releasably joined by any number of means such as double-sided tape or releasable fasteners. Other means of achieving the release of wetness to a controlled extent would be appreciated by those skilled in the art.

Although preferred embodiments of the invention have been described herein in detail, it will be understood by those skilled in the art that variations may be made thereto without departing from the spirit of the invention or the scope of the appended claims.

I claim:

1. A disposable training panty adapted to release wetness to a controlled extent, comprising:
   (a) an outer liquid permeable covering including a front portion and a back portion, said front and back portions being contiguous along a crotch area,
   (b) an inner absorbent portion secured to said outer covering which does not fully absorb a child's wetness so that in the event the child has a bowel or bladder accident in said panty said panty releases through said permeable covering to said controlled extent unabsorbed wetness,
   (c) means for joining the sides of said front and back portions to form side seam, said joining means being releasable to permit ready opening of said seams in the event the child has a bowel or bladder accident in said panty,
   (d) means for securing said panty to a child's waist, and
   (e) means for defining leg openings through which a child's legs will extend once said panty is secured to a child.

2. A disposable panty of claim 1 wherein the width of said inner absorbent portion is narrower than the width of said crotch area and extends in length beyond the crotch area along said front and back portions, said absorbent portion having side portions spaced apart from said means for defining said leg openings.

3. A disposable panty of claim 1 wherein said joining means comprises:
   (a) loosely basting a pair of ties through said front and back portions to form said side seam;
   (b) means for securing said ties to said panty; and
   (c) means for ready removal of said ties.

4. A disposable panty of claim 3 wherein said means for securing said ties is a bow tied at one end of said ties and said means for ready removal is a knot tied at the other end of said ties.

5. A disposable panty of claim 1 wherein said joining means is velcro.

6. A disposable training panty adapted to release wetness to a controlled extent, comprising:
   (a) an outer permeable covering including a front portion and a back portion, said front and back portions being contiguous along a crotch area;
   (b) an inner absorbent portion secured to said outer covering which does not fully absorb a child's wetness so that in the event the child has a bowel or bladder accident in said panty said panty releases through said permeable covering to said controlled extent unabsorbed wetness;
   (c) means for joining the sides of said front and back portions to form side seams, said joining means being releasable to permit ready opening of said seams in the event the child has a bowel or bladder accident in said panty;
   (d) means for securing said panty to a child's waist; and
   (e) means for defining leg openings through which a child's legs will extend once said panty is secured to a child; wherein said joining means comprises:
   (f) a pair of ties loosely basted through said front and back portions to form said side seam;
   (g) means for securing said ties to said panty; and
   (h) means for ready removal of said ties.

7. A disposable panty of claim 6 wherein said means for securing said ties is a bow tied at one end of said ties and said means for ready removal is a knot tied at the other end of said ties.

* * * * *